US00PP26605P2

(12) United States Plant Patent
Heemskerk

(10) Patent No.: US PP26,605 P2
(45) Date of Patent: Apr. 12, 2016

(54) ***HEMEROCALLIS* PLANT NAMED 'VER00213'**

(50) Latin Name: ***Hemerocallis* hybrid**
Varietal Denomination: VER00213

(71) Applicant: Gerardus J. C. M. Heemskerk, Noordwijk (NL)

(72) Inventor: Gerardus J. C. M. Heemskerk, Noordwijk (NL)

( * ) Notice: Subject to any disclaimer, the term of this patent is extended or adjusted under 35 U.S.C. 154(b) by 0 days.

(21) Appl. No.: 14/544,488

(22) Filed: Jan. 12, 2015

(51) Int. Cl.
*A01H 5/02* (2006.01)

(52) U.S. Cl.
USPC ..... Plt./312

(58) Field of Classification Search
USPC ..... Plt./263.1, 312
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hemerocallis* named 'VER00213' that is characterized by its bicolored flowers with petals that are light to dark salmon pink with a slightly darker halo, light salmon sepals, and yellow throat, its everblooming habit; blooming from June to October in The Netherlands, its compact and dormant plant habit, and its vigorous growth habit.

2 Drawing Sheets

Botanical classification: *Hemerocallis* hybrid.
Cultivar designation: 'VER00213'.

BACKGROUND OF THE INVENTION

The present invention relates to a new and distinct cultivar of *Hemerocallis* plant of hybrid origin, botanically known as *Hemerocallis* 'VER00213' and will be referred to hereafter by its cultivar name, 'VER00213'.

The new cultivar was developed through an on-going breeding program conducted by the Inventor in Noordwijk, The Netherlands. The objectives of the breeding program are to develop new cultivars of *Hemerocallis* that are everblooming with compact plant habits in a range of flower colors.

The new cultivar arose from crosses made in summer of 2006. Proprietary seed parent lines were pollinated with a mixture of pollen collected from proprietary pollen parents and the collected seeds were pooled and sown for evaluation. 'VER00213' was selected as a single unique plant from the resulting seedlings in summer of 2009. The specific parents are unknown and none of the possible parent plants are named or patented.

Asexual propagation of the new cultivar was first accomplished by division in Noordwijk, The Netherlands in 2009 by the Inventor. Asexual propagation by division and tissue culture has determined that the characteristics of this cultivar are stable and are reproduced true to type in successive generations.

SUMMARY OF THE INVENTION

The following traits have been repeatedly observed and represent the characteristics of 'VER00213'. These attributes in combination, distinguish 'VER00213' as a new and distinct cultivar of *Hemerocallis*.

1. 'VER00213' exhibits bicolored flowers with petals that are light to dark salmon pink with a slightly darker halo, light salmon sepals, and yellow throat.

2. 'VER00213' exhibits an everblooming habit; blooming from June to October in The Netherlands.
3. 'VER00213' exhibits a compact and dormant plant habit.
4. 'VER00213' exhibits a vigorous growth habit.

The new cultivar can be most closely compared to the *Hermeocallis* hybrid cultivars 'Little Anna Rosa' (not patented) and 'Pretty Fancy' (not patented). 'Little Anna Rosa' is similar to 'VER00213' in having a compact plant habit. 'Little Anna Rosa' differs from 'VER00213' in having flowers with petal that are faded in color towards the margin, in having a short flowering period, in having a green colored throat, and in having an evergreen plant habit. 'Pretty Fancy' is similar to 'VER00213' in having a dormant plant habit. 'Pretty Fancy' differs from 'VER00213' in having a shorter flowering period and in having a taller flower scape.

BRIEF DESCRIPTION OF THE DRAWINGS

The accompanying colored photographs illustrate the overall appearance and distinct characteristics of the new *Hemerocallis*. The photographs were taken of a 6 month-old plant of the new cultivar as field grown in Noordwijk, The Netherlands and placed in a container for the photographs.

The photograph in FIG. 1 provides a side view of 'VER00213' in bloom.

Figure 1:
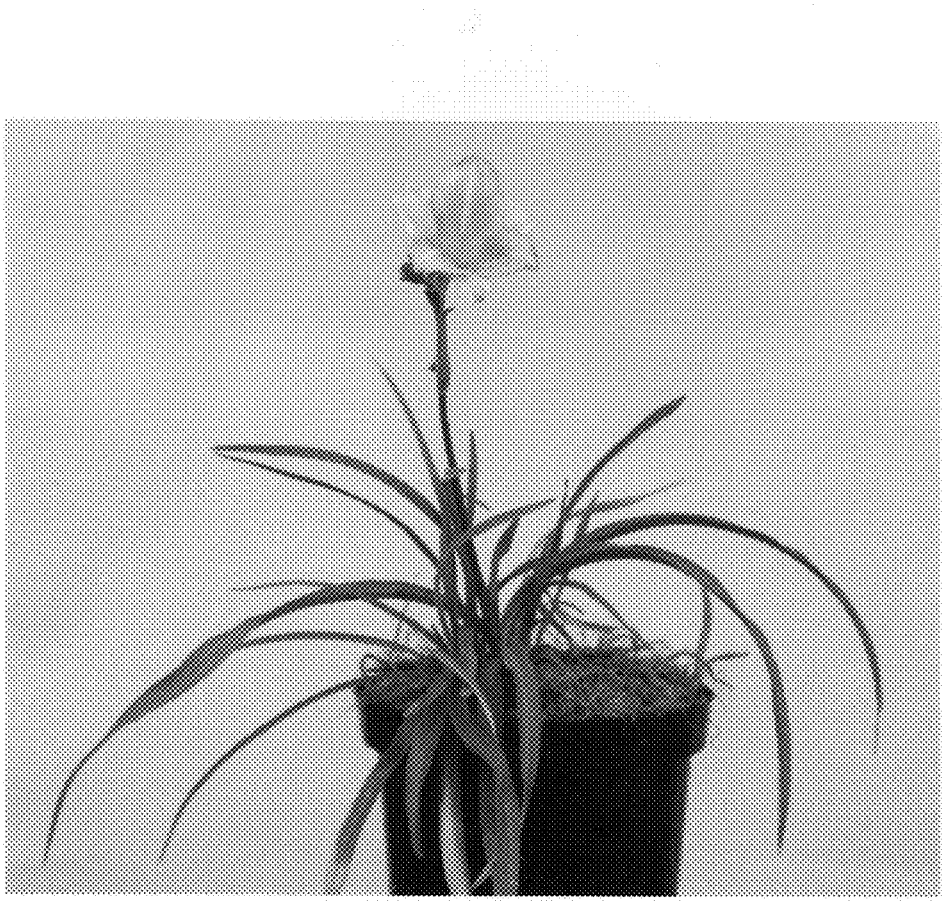
Figure 2:
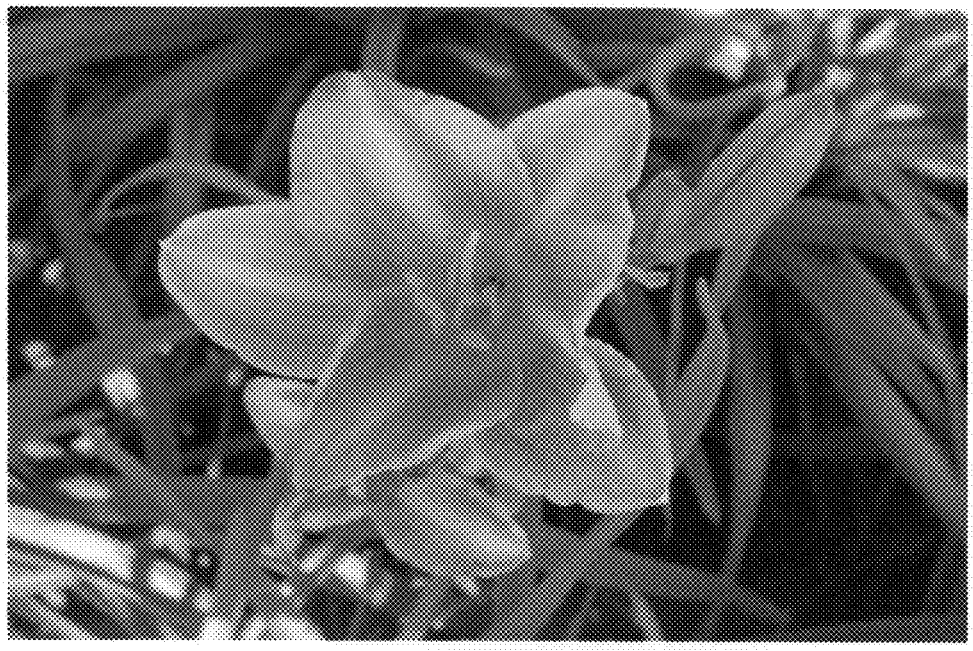

The photograph in FIG. 2 provides a close-up view of a flower and a flower bud of 'VER00213'.

Figure 3:
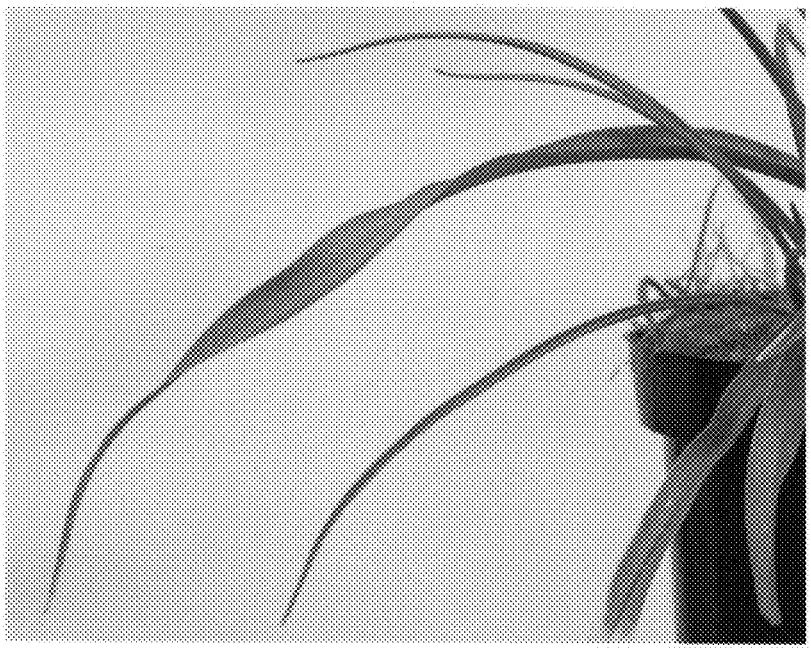

The photograph in FIG. 3 provides a close-up view of the foliage of 'VER00213'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 6 month-old plants of the new cultivar as field grown in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Everblooming from June to October in The Netherlands.

*Plant type*.—Herbaceous perennial, dormant type.

*Plant habit*.—Compact, basal rosette, grass-like foliage.

*Height and spread*.—An average of 30 cm in height to top of foliage and 47.7 cm in height to top of inflorescence and 37.8 cm in spread (after two years in the garden).

*Hardiness*.—At least in U.S.D.A. Zone 5.

*Diseases*.—No disease resistance or susceptibility has been observed.

*Root description*.—Fibrous roots.

*Propagation*.—Division and tissue culture.

*Growth rate*.—Vigorous.

*Stem description*.—Basal rosette, no lateral branches present.

Foliage description:

*Leaf shape*.—Linear, carinate, curved and slightly twisted.

*Leaf division*.—Simple.

*Leaf base*.—Decurrent.

*Leaf apex*.—Long acute with a short apiculate tip.

*Leaf venation*.—Parallel, color upper surface; 137C and lower surface; 143A.

*Leaf margins*.—Entire, slightly undulate.

*Leaf attachment*.—Decurrent, no petioles.

*Leaf arrangement*.—Basal rosette.

*Leaf orientation*.—Held upright to broadly-spreading and recurved.

*Leaf surface*.—Both surfaces glabrous, upper surface slightly glossy, lower surface dull.

*Leaf color*.—Young leaves upper surface; color between 143A to 143B, ung leaves lower surface; 143B, mature leaves upper surface; 137C, mature leaves lower surface; color between 143A and 146A.

*Leaf size*.—An average of 29.4 cm in length and 1.3 cm in width.

*Leaf quantity*.—Average of 14 per rosette.

Flower scape description (peduncle):

*Scape shape*.—Slightly flattened.

*Scape number*.—1 per basal rosette at one time continuously produced during bloom season.

*Scape aspect*.—Straight, held at an average angle of 80° to soil level.

*Scape size*.—An average of 27.5 cm in length and 4 mm in diameter.

*Scape color*.—144B.

*Scape surface*.—Glabrous and dull.

*Scape branching*.—None.

Flower description:

*Inflorescence type*.—Scape bearing a terminal panicle of single flowers.

*Inflorescence size*.—An average of 8.4 cm in width and 13.8 cm in depth.

*Lastingness of flowers*.—About 24 hours, self cleaning.

*Flower size*.—An average of 7.9 cm in depth and 6.5 cm in diameter.

*Flower fragrance*.—None detected.

*Flower shape*.—Campanulate, single.

*Flower number*.—An average of 12 flowers and buds per scape.

*Flower aspect*.—Upright to outward.

*Flower bud*.—Oblanceolate in shape, an average of 5.3 cm in length and 1.3 cm in width, color; N144D tinged 16B with top 144B.

*Rate of flower opening*.—About 10% of flowers open at a time, about 4 weeks for all flowers to open per scape.

*Flower attachment*.—Pedicellate.

*Petals*.—3, obovate shape, an average of 7.3 cm in length and 3.6 cm in width, margins entire and very slightly crinkled, apex broadly acute and slightly curved, base fused (lower 18%), both surfaces glabrous, dull, and slightly velvety, color; upper surface when opening and when fully open; 171D (halo slightly darker) with base 16A, center stripe 19C (main vein), and tube (throat) 11B, lower surface when opening and when fully open; 22C to 22D with margins N170D and tube 154C, color not fading.

*Sepals*.—3, rotate in arrangement, average of 7.3 cm in length, 2.2 cm in width, oblanceolate in shape, entire margins, base cuneate with lower portion fused (18%), acute apex, color; upper surface when opening and when fully open; 19A with margins 22A to 22B and tube 11B, lower surface when opening and when fully open; 22A with margins 23D, tip 143A and tube 154C, both surfaces glabrous, matte, and slightly velvety.

*Calyx*.—Rotate in arrangement, an average of 4.7 cm in length and 6.5 cm in diameter.

*Pedicels*.—An average of 4 mm in length and 0.2 mm in diameter, strong strength, color; 143C, held at an angle of 40° to peduncle, glabrous surface.

*Pedicel leaf*.—Average of 1 per pedicel, broadly lanceolate in shape, 144A in color on both surfaces, average of 3 cm in length and 1 cm in width, sheathed base, narrowly acuminate apex, glabrous on both surfaces.

Reproductive organs:

*Gynoecium*.—Pistil; 1, style; 6.4 cm in length, 26D with 150D at the base in color, stigmas; crested, 158D in color, 1 mm in length, ovary; oblong in shape, 144A in color.

*Androecium*.—Stamens; 6, anthers; narrowly oblong in shape, dorsifixed, 5 mm in length and 148D in color; filament; 3.4 cm in length, 22A in color, pollen; moderate to high in quantity and 13B in color.

*Fruit/seeds*.—None observed.

It is claimed:

1. A new and distinct cultivar of *Hemerocallis* plant named 'VER00213' as herein illustrated and described.

* * * * *